United States Patent [19]

Fletcher

[11] 4,190,590

[45] Feb. 26, 1980

[54] AZIDE AND ISOCYANATE DERIVATIVES OF 2-NITRO-3-PHENYLBENZOFURAN

[75] Inventor: Vernon R. Fletcher, Davis, Calif.

[73] Assignee: Riker Laboratories, Inc., Northridge, Calif.

[21] Appl. No.: 973,152

[22] Filed: Dec. 26, 1978

[51] Int. Cl.$^2$ .................. C07D 307/82; C07D 307/84
[52] U.S. Cl. ................................................ 260/346.73
[58] Field of Search ..................................... 260/346.73

[56] References Cited

U.S. PATENT DOCUMENTS

| 3,862,134 | 1/1975 | Scherrer | 260/346.22 |
| 4,048,323 | 9/1977 | Scherrer | 260/346.22 |
| 4,066,782 | 1/1978 | Scherrer | 260/346.22 |
| 4,067,993 | 1/1978 | Scherrer | 260/346.22 |
| 4,124,704 | 11/1978 | Scherrer | 260/346.22 |

Primary Examiner—Alan L. Rotman
Assistant Examiner—Bernard Dentz
Attorney, Agent, or Firm—Cruzan Alexander; Donald M. Sell; Donald C. Gipple

[57] ABSTRACT

2-Nitro-3-phenylbenzofurans wherein the benzo or 3-phenyl portion of the molecule is bonded directly to an azide or an isocyanate group.

7 Claims, No Drawings

AZIDE AND ISOCYANATE DERIVATIVES OF 2-NITRO-3-PHENYLBENZOFURAN

BACKGROUND OF THE INVENTION

This invention relates to a class of 2-nitro-3-phenylbenzofuran compounds wherein the benzo or 3-phenyl portion of the molecule is bonded directly to an azide or an isocyanate group. These compounds are intermediates in the preparation of certain active antimicrobial agents.

Compounds wherein 2-nitro-3-phenylbenzofuran is substituted by certain neutral or acidic groups are known. See, for example, U.S. Pat. Nos. 4,022,908; 4,048,323; 4,066,782; 4,067,993 and 4,124,704. No previous disclosure of compounds wherein the benzo or 3-phenyl portions of 2-nitro-3-phenylbenzofurans is substituted by an azide or an isocyanate group are known, however.

DETAILED DESCRIPTION OF THE INVENTION

The present invention relates to a class of compounds of the formula

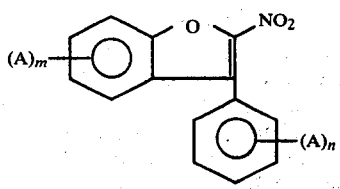
(I)

wherein A is OCN— or

, m and n are zero or one and the sum of m and n is one. These compounds are intermediates in the preparation of certain aromatic amine-substituted 2-nitro-3-phenylbenzofurans, which are active antimicrobial agents (particularly antibacterial agents). The aromatic amine-substituted compounds are the subject of a commonly-assigned patent application of Robert A. Scherrer, Richard M. Stern and Vernon R. Fletcher, filed of even date herewith Ser. No. 973,153. The disclosure of that application is incorporated herein by reference.

The isocyanate compounds of the invention:

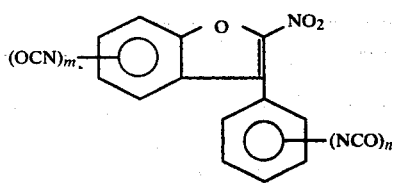
(II)

are prepared by pyrolysis of the corresponding azide compounds of the invention:

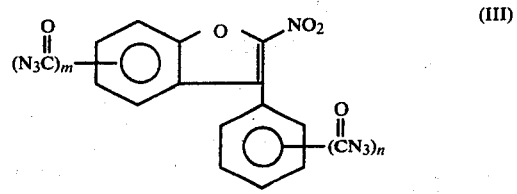
(III)

in an inert solvent such as toluene, as shown in Examples 1 and 2 hereof. The azides (III) are themselves prepared from 2-nitro-3-phenylbenzofurancarboxylic acids or (2-nitro-3-phenylbenzofuranyl)benzoic acids (described in U.S. Pat. Nos. 4,048,323 and 4,067,993) by reaction with thionyl chloride to provide the carboxyl chlorides followed by reaction with sodium azide to provide the corresponding azides.

The aromatic amine-substituted 2-nitro-3-phenylbenzofuran antimicrobial agents which are prepared from the corresponding isocyanates (II) can be represented by the formula

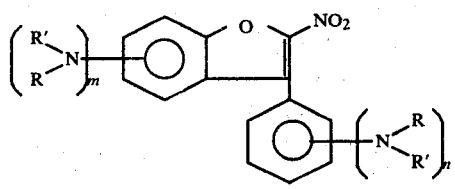
(IV)

wherein m and n are as previously defined and

is a substituted or unsubstituted amine group (in which R is hydrogen or a lower alkyl group and R' can be R or any of a variety of cyclic, alicyclic or non-cyclic groups). Such compounds in which

is a ureido group can be prepared by reaction of the corresponding isocyanate II with primary and secondary amines. The carbamoyl-substituted compounds IV can be prepared by reaction of the corresponding isocyanate II with lower alkyl alcohols and the primary amino (H$_2$N-)-substituted compounds IV can be prepared from the corresponding isocyanate II in the presence of water, utilizing the Curtius rearrangement.

The antimicrobial activity of the compounds IV is evaluated using a variation of the original agar-plate diffusion method of Vincent and Vincent (e.g. see Vincent, J. G., and Vincent, Helen W., Proc. Soc. Exptl. Biol. Med. 55:162–164, 1944, and Davis, B. D., and Mingioli, E. S., J. Bac. 66:129–136, 1953). Using this test, they have a broad spectrum of activity against both gram-positive and gram-negative microorganisms (particularly bacteria).

The following examples are given for the purpose of illustrating the invention, but are in no way limiting thereof. The melting points are uncorrected and are in degrees Centigrade. Examples 1 and 2 relate to the preparation of compounds of the invention, and Examples 3-8 relate to the preparation of active antimicrobial agents IV therefrom.

EXAMPLE 1

Step A

A sample of 2-nitro-3-phenylbenzofuran-7-carboxylic acid is reacted with thionyl chloride to provide 2-nitro-3-phenylbenzofuran-7-carboxyl chloride. A solution of 9 g. (0.0298 mole) of the chloride in 270 ml. of acetone is treated with 4.5 g. (0.069 mole) of sodium azide dissolved in 15 ml. of water. The mixture is stirred at 20° C. for 3 hours, then poured into 600 ml. of water. The resulting yellow precipitate is separated by filtration, washed with water and dried. This product, 2-nitro-3-phenylbenzofuran-7-azide, melts with decomposition at 133° C.

Step B

A mixture of 9.5 g. of the azide product from Step A with 175 ml. of toluene is slowly heated to 100°–110° C. whereupon a gas evolution occurs. At the end of the gas evolution, the mixture is heated and maintained at reflux for 15 minutes. The solvent is then removed by evaporation to provide a yellow solid residue of 2-nitro-3-phenylbenzofuran-7-isocyanate.

EXAMPLE 2

Step A

A mixture of 40.5 g. (0.43 mole) of phenol, 100 g. (0.428 mole) of 4-chloro-α-bromoacetophenone, 100 g. (0.725 mole) of potassium carbonate and 500 ml. of glyme is heated to its reflux temperature and maintained at reflux for about 6 hours. The reaction mixture is evaporated to remove the solvent. The residue is diluted with water and diethyl ether, and the layers are separated. The ether layer is washed with water and saturated sodium chloride solution and dried over magnesium sulfate. The ether solution is evaporated to provide a dark oil which gradually solidifies on cooling. The solid is recrystallized from ethanol to provide 4-chloro-α-phenoxyacetophenone, m.p. 81°–86° C.

Step B

A mixture of 350 g. of polyphosphoric acid and 51.3 g. (0.208 mole) of 4-chloro-α-phenoxyacetophenone is heated to a temperature of about 80° C. and maintained at this temperature for about 1 hour. The reaction mixture is then poured into cold water. The yellow product is collected, washed with water and dissolved in diethyl ether. The ether solution is washed with cold dilute sodium hydroxide solution, water and saturated sodium chloride solution, then dried over sodium sulfate. The solvent is evaporated to provide a dark oil which solidifies to 3-(4-chlorophenyl)benzofuran. The structural assignment is supported by infrared spectral analysis.

Step C

A mixture of 45.2 g. (0.198 mole) of 3-(4-chlorophenyl)benzofuran, 22.2 g. (0.248 mole) of cuprous cyanide and 15 ml. of pyridine is heated to 220° C. and maintained at this temperature for one day. The mixture is then poured into a solution of 47.5 g. of ferric chloride, 30 ml. of concentrated hydrochloric acid and 135 ml. of water with stirring. The mixture is stirred with heating below its boiling point for 1 hour. The aqueous portion is removed, and the organic portion is mixed with 1.2 liter of benzene, and the mixture is stirred for 1 hour. The mixture is then filtered. The filtrate is washed with 6 N hydrochloric acid, water, 10 percent sodium hydroxide solution and saturated sodium chloride solution, then dried over magnesium sulfate. The benzene solution is then evaporated to provide a dark oil which solidifies to provide 3-(4-cyanophenyl)benzofuran. The infrared spectrum of the product is consistent with the assigned structure.

Step D

A mixture of 24.4 g. (0.111 mole) of 3-(4-cyanophenyl)benzofuran, 25 g. of 85 percent potassium hydroxide and 250 ml. of 95 percent aqueous ethanol is heated to its reflux temperature and maintained at reflux for 15 hours. The solvent is removed by evaporation, and the residue is diluted with water and diethyl ether. The solid precipitate is separated and dissolved in 800 ml. of hot water. This aqueous solution is then acidified with 6 N hydrochloric acid to provide a white precipitate which is collected by filtration and washed with water. The white product is then recrystallized from 1,2-dichloroethane to provide 4-(3-benzofuranyl)benzoic acid, m.p. 222°–225° C.

| Analysis: | %C | %H |
|---|---|---|
| Calculated for $C_{15}H_{11}O_3$: | 75.6; | 4.24 |
| Found: | 75.6; | 4.10. |

Step E

A stirred solution of 14 g. (0.059 mole) of 3-(3-benzofuranyl)benzoic acid and 1500 ml. of 1,2-dichloroethane which has been heated to its reflux temperature is slowly cooled to about 60° C. and treated dropwise with 9.4 g. (0.059 mole) of bromine diluted with 7 ml. of 1,2-dichloroethane. After stirring the mixture for about 50 hours at about 55° C., the reaction mixture is cooled, and the solid precipitate is collected and rinsed with 1,2-dichloroethane. Infrared spectral analysis of the crude product, 4-(2-bromo-3-benzofuranyl)benzoic acid, is consistent with the assigned structure. The crude product has a melting point of 218°–220° C.

Step F

A mixture of 18.7 g. (0.059 mole) of 4-(2-bromo-3-benzofuranyl)benzoic acid and 1200 ml. of acetic acid is warmed to 65° C. and 7.5 g. (0.089 mole) of cyclohexene is added, then 8.2 g. (0.089 mole) of dinitrogen tetraoxide diluted with 20 ml. of acetic acid is added dropwise. After stirring for about 3 hours, the reaction mixture is poured into cold water, and the solid precipitate is collected and washed with water and petroleum ether. The product is recrystallized from a mixture of N,N-dimethylformamide and water and from glyme and water. The product is 4-(2-nitro-3-benzofuranyl)benzoic acid, m.p. 274°–278° C.

| Analysis: | %C | %H | %N |
|---|---|---|---|
| Calculated for $C_{15}H_9NO_5$: | 63.6; | 3.2; | 4.9 |
| Found: | 63.2; | 3.2; | 5.2. |

Step G

Using the method of Example 1, Step A, 4-(2-nitro-3-benzofuranyl)benzoic acid is reacted with thionyl chloride to provide the corresponding benzoyl chloride which is further reacted with sodium azide to provide 4-(2-nitro-3-benzofuranyl)phenyl azide.

Step H

Using the method of Example 1, Step B, the azide intermediate of Step G above is converted to 4-(2-nitro-3-benzofuranyl)phenyl isocyanate.

EXAMPLE 3

To a solution of 2-nitro-3-phenylbenzofuran-7-isocyanate (the product of Example 1) in toluene is added a large excess of methanol. The solution is stirred for about 15 minutes, then evaporated to provide a yellow crystalline residue which is recrystallized from ethanol to provide yellow needles of 7-(methyl carbamoyl)-2-nitro-3-phenylbenzofuran, m.p. 167°–169° C.

| Analysis: | %C | %H | %N |
|---|---|---|---|
| Calculated for $C_{16}H_{12}O_5N_2$: | 61.5; | 3.9; | 9.0 |
| Found: | 61.0; | 4.0; | 9.0. |

EXAMPLE 4

A solution of 2-nitro-3-phenylbenzofuran-7-isocyanate is prepared from 3.5 g. of the corresponding azide by heating in 25 ml. of toluene at a bath temperature of 105° C., then refluxing for 10 minutes. To one-third of this isocyanate solution is added 20 ml. of pyrrolidine. After 1 hour of stirring, the solvent is removed by evaporation to provide a yellow residue which is recrystallized from methanol to provide 1,1-tetramethylene-3-[7-(2-nitro-3-phenylbenzofuranyl)]urea, m.p. 215°–216° C., having the structure

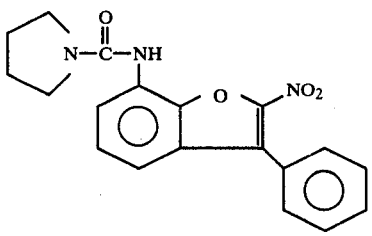

| Analysis: | %C | %H | %N |
|---|---|---|---|
| Calculated for $C_{19}H_{17}N_3O_4$: | 65.0; | 4.9; | 12.0 |
| Found: | 64.9; | 4.8; | 11.9. |

EXAMPLE 5

To a 25 ml. portion of the solution of 2-nitro-3-phenylbenzofuran-7-isocyanate from Example 4 is added 2 ml. of n-butylamine. The mixture is stirred for 1 hour, then evaporated to provide a residue which is recrystallized from aqueous methanol. The product is 1-(1-butyl)-3-[7-(2-nitro-3-phenylbenzofuranyl)]urea, m.p. 194°–196.5° C. having the structure

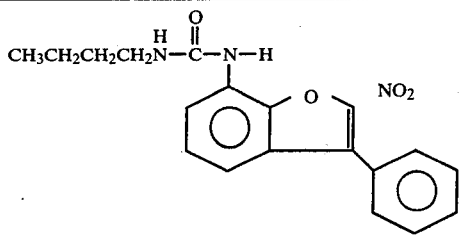

| Analysis: | %C | %H | %N |
|---|---|---|---|
| Calculated for $C_{19}H_{19}N_3O_4$: | 64.6; | 5.4; | 11.9 |
| Found: | 64.6; | 5.2; | 11.7. |

EXAMPLE 6

To the remaining ⅔ of the solution from Example 4 which consists of 25 ml. of a toluene solution of 2-nitro-3-phenylbenzofuran-7-isocyanate is added 2 ml. of N-methylpiperazine. After stirring for 1 hour the reaction mixture is evaporated to provide a residue which gradually solidifies. The crude material is recrystallized to provide yellow crystals of 1,1-[3-(N-methyl)azapentamethylene]-3-[2-nitro-3-phenylbenzofuranyl]urea, m.p. 162°–163° C., having the structure

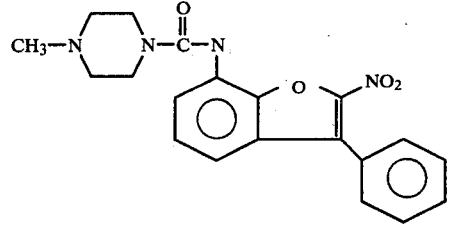

| Analysis: | %C | %H | %N |
|---|---|---|---|
| Calculated for $C_{20}H_{20}N_4O_4$: | 63.2; | 5.3; | 14.7 |
| Found: | 63.0; | 5.2; | 14.6. |

EXAMPLE 7

The isocyanate from Example 1 is dissolved in 100 ml. of glyme and to this solution is added 30 ml. of concentrated hydrochloric acid previously saturated with hydrogen chloride gas. The mixture is stirred and heated to about 70°–80° C., gas evolution occurs and, after this ends, the reaction mixture is allowed to cool gradually to about 20° C. Upon cooling, some solid separates, but the reaction mixture is neutralized with sodium carbonate. The resulting solution is extracted with diethyl ether, the ether solution is washed with water, then dried and the ether is evaporated. The resulting orange solid is recrystallized from aqueous ethanol to provide 7-amino-2-nitro-3-phenylbenzofuran, m.p. 164°–166° C.

| Analysis: | %C | %H | %N |
|---|---|---|---|
| Calculated for $C_{14}H_{10}N_2O_3$: | 66.1; | 3.96; | 11.0 |
| Found: | 66.4; | 3.8; | 10.9. |

EXAMPLE 8

Using the method of Example 5, 4-(2-nitro-3-benzofuranyl)phenyl isocyanate (the product of Example 2) is reacted with n-propylamine to provide 1-(1-propyl)-3-[4-(2-nitro-3-benzofuranyl)phenyl]urea having the structure

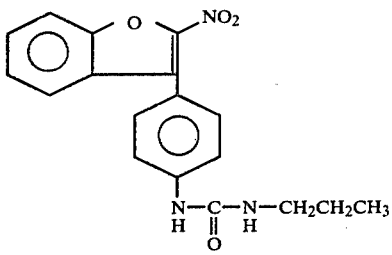

The products of Examples 3–8 are active antimicrobial agents and are all useful in vitro and topically against bacteria. Thus, they can be used for disinfecting and sterilizing, for example, medical and dental equipment, as components of disinfecting solutions.

What is claimed is:

1. A compound of the formula

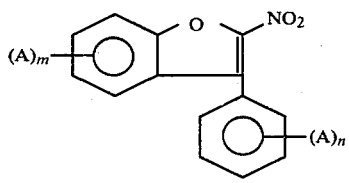

wherein A is OCN— or

and m and n are zero or one and the sum of m and n is one.

2. A compound of the formula

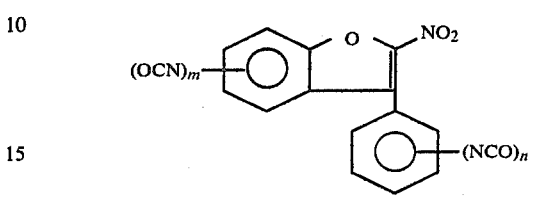

wherein m and n are zero or one and the sum of m and n is one.

3. 2-Nitro-3-phenylbenzofuran-7-isocyanate according to claim 2.

4. 4-(2-Nitro-3-benzofuranyl)phenyl isocyanate according to claim 2.

5. A compound of the formula

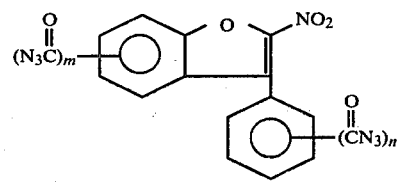

wherein m and n are zero or one and the sum of m and n is one.

6. 2-Nitro-3-phenylbenzofuran-7-azide according to claim 5.

7. 4-(2-Nitro-3-benzofuranyl)phenyl azide according to claim 5.

* * * * *